US007878959B2

(12) United States Patent
Chen et al.

(10) Patent No.: US 7,878,959 B2
(45) Date of Patent: Feb. 1, 2011

(54) ELECTRICALLY OPERATED REHABILITATION AND EXERCISE BED FOR SIMULTANEOUS TRACTION OF UPPER LIMBS AND LOWER LIMBS

(76) Inventors: Ko-Chuan Chen, 18F-3, No. 384, Min-An West Road, Hsin-Chuang City, Taipei County (TW); Kuan-Chih Chen, 18F-3, No. 384, Min-An West Road, Hsin-Chuang City, Taipei County (TW); Kuan-Han Chen, 18F-3, No. 384, Min-An West Road, Hsin-Chuang City, Taipei County (TW)

( * ) Notice: Subject to any disclaimer, the term of this patent is extended or adjusted under 35 U.S.C. 154(b) by 0 days.

(21) Appl. No.: 12/583,799

(22) Filed: Aug. 27, 2009

(65) Prior Publication Data

US 2010/0113232 A1 May 6, 2010

(30) Foreign Application Priority Data

Oct. 31, 2008 (TW) ............................ 97219467 U

(51) Int. Cl.
*A63B 26/00* (2006.01)
*A63B 22/12* (2006.01)
*A63B 21/00* (2006.01)
*A61F 5/00* (2006.01)

(52) U.S. Cl. ......................... 482/142; 482/62; 482/133; 602/33

(58) Field of Classification Search .................. 482/10, 482/95, 96, 133, 142, 57, 60, 62; 602/31-36, 602/37-40; 5/612, 662; 128/845
See application file for complete search history.

(56) References Cited

U.S. PATENT DOCUMENTS

| | | | | |
|---|---|---|---|---|
| 1,612,496 | A * | 12/1926 | Dobbins | 482/131 |
| 2,262,271 | A * | 11/1941 | De Camp | 601/26 |
| 5,820,519 | A * | 10/1998 | Slenker | 482/4 |
| 6,228,004 | B1 * | 5/2001 | Steinbach et al. | 482/121 |
| 6,685,605 | B1 * | 2/2004 | Klossner | 482/142 |
| 7,137,959 | B2 * | 11/2006 | Phillips | 601/5 |
| 2008/0113853 | A1 * | 5/2008 | Jang | 482/142 |
| 2010/0144504 | A1 * | 6/2010 | Krell | 482/143 |

* cited by examiner

*Primary Examiner*—Allana Lewin

(57) ABSTRACT

A rehabilitation and exercise bed includes: a bed having a driving motor provided under the bed; a rotary traction device having a right and a left pedal respectively secured to a pair of crank arms rotatably mounted on opposite ends of an axial shaft of the driving motor for rehabilitating or exercising a patient's feet in a rotary movement like pedaling a bicycle; a lower-limb traction device connected to a front portion of the rotary traction device for reciprocatively rehabilitating or exercising the patient's lower limbs; and an upper-limb traction device connected to a rear portion of the rotary traction device for reciprocatively exercising the patient's upper limbs.

5 Claims, 6 Drawing Sheets

ELECTRICALLY OPERATED REHABILITATION AND EXERCISE BED FOR SIMULTANEOUS TRACTION OF UPPER LIMBS AND LOWER LIMBS

BACKGROUND OF THE INVENTION

U.S. Pat. No. 5,181,289 disclosed a bed apparatus and rehabilitation attachment, in which a rope is extended around a pulley so that a sick person can alternately pull the ends of the rope with hands for exercising the hands. The person's feet may be connected to one end of the rope while pulling the other end of the rope with hands for exercising the person's limbs.

However, it may only exercise the patient's limbs by lifting the feet upwardly and then releasing the feet downwardly. There is no mechanism of rotary motion for exercising the lower limbs in a rotational way like pedaling a bicycle. When lifting or lowering the lower limbs by such a prior art, the patient's lower back or hip portion will be subjected to pressure due to lower body weight, thereby easily causing a pressure or bed sore at the lower back portion after a long time exercise.

The present inventor has found the drawbacks of the prior art and invented the present rehabilitation and exercise bed for traction of the upper and lower limbs either in reciprocating movement or in a rotary motion.

SUMMARY OF THE INVENTION

The object of the present invention is to provide a rehabilitation and exercise bed including: a bed having a driving motor provided under the bed; a rotary traction device having a right and a left pedal respectively secured to a pair of crank arms rotatably mounted on opposite ends of an axial shaft of the driving motor for rehabilitating or exercising a patient's feet in a rotary movement like pedaling a bicycle; a lower-limb traction device connected to a front portion of the rotary traction device for reciprocatively rehabilitating or exercising the patient's lower limbs; and an upper-limb traction device connected to a rear portion of the rotary traction device for reciprocatively exercising the patient's upper limbs.

DETAILED DESCRIPTION

Figure 1:
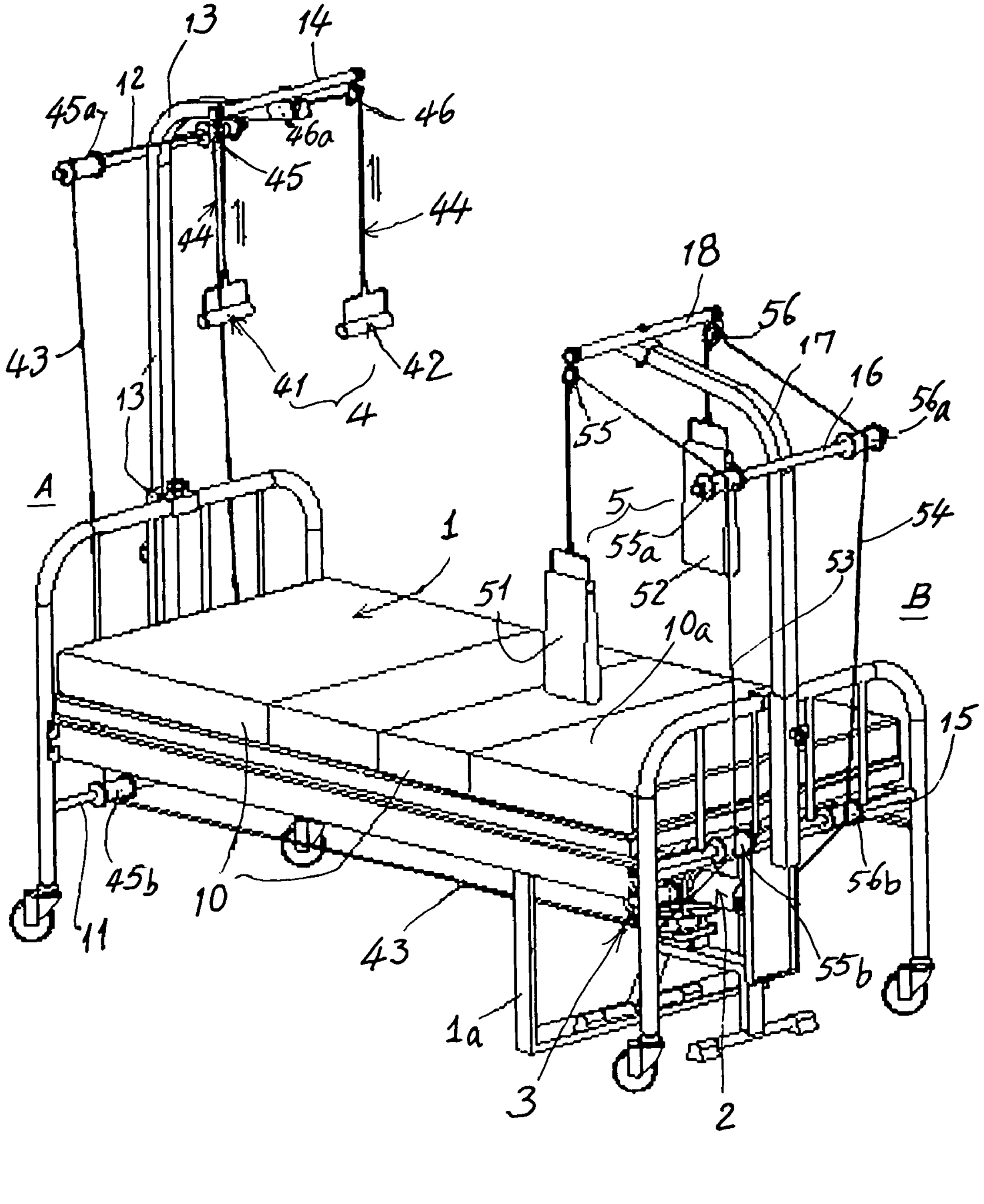
FIG. 1 is a perspective view of the present invention.
Figure 2:
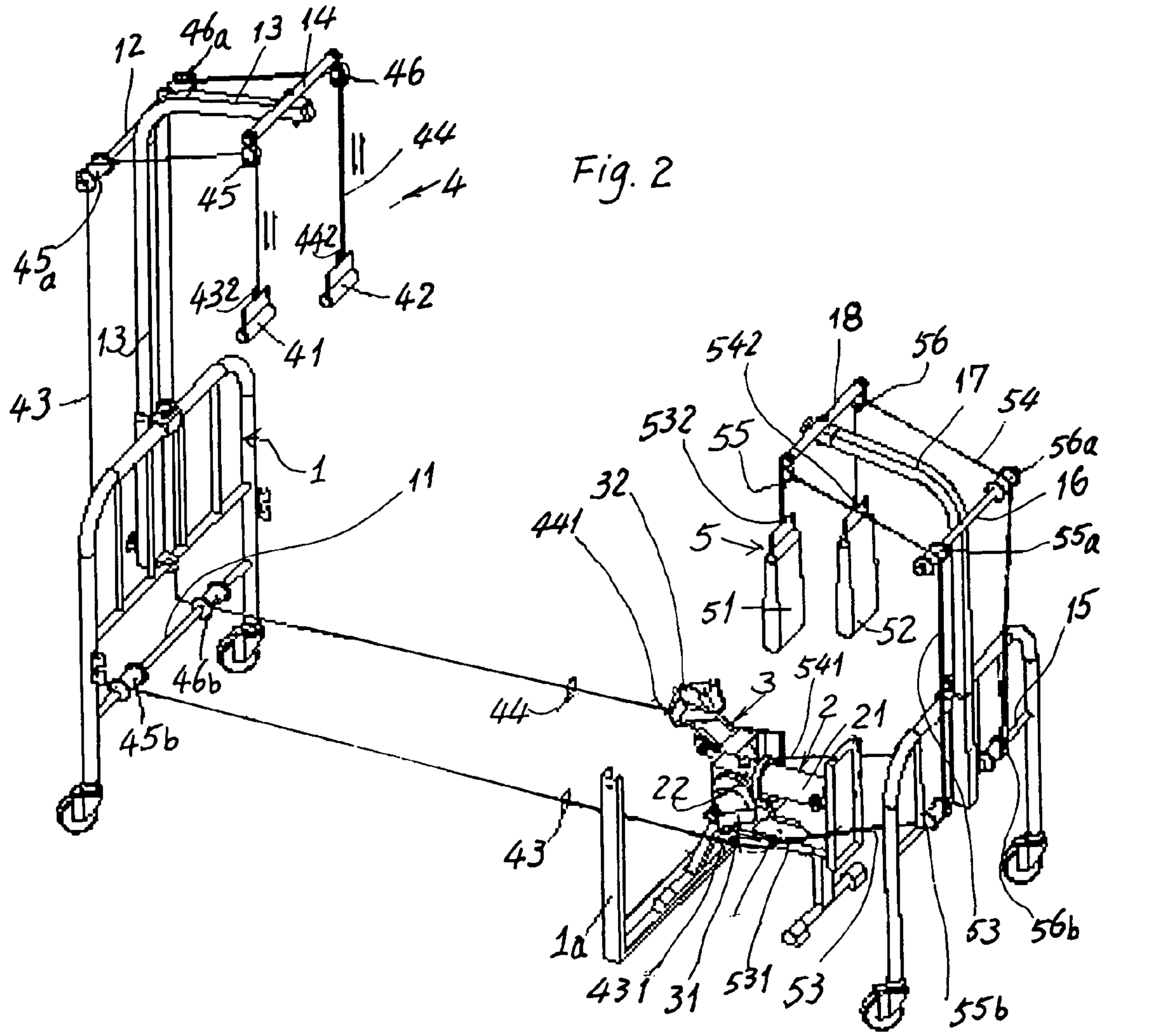
FIG. 2 shows the detailed structure of the present invention when removing the bed mattress.
Figure 3:
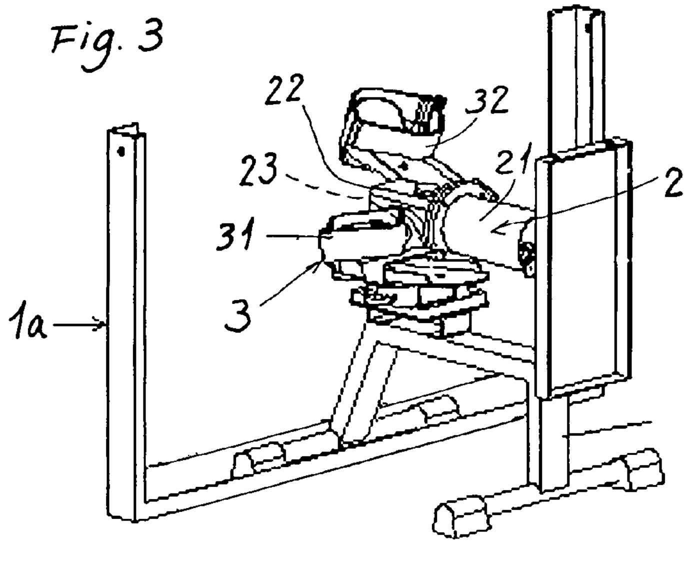
FIG. 3 is a perspective view of the driving means and rotary traction means of the present invention.
Figure 4:
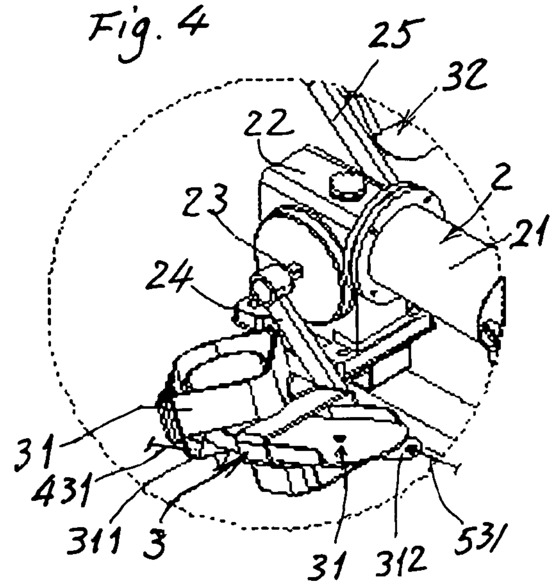
FIG. 4 is a perspective view partially showing a right portion of the driving means and the rotary traction means.
Figure 5:
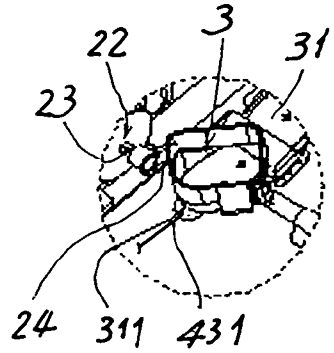
FIG. 5 shows a partial rear portion of the rotary traction means and driving means.

As shown in the drawing figures, the rehabilitation and exercise bed of the present invention comprises: a bed 1; a driving means 2 mounted on a bottom portion of the bed 1 adjacent to a patient's feet side B; a rotary traction means 3 connected to and rotatably driven by the driving means 2 for rotatably exercising or rehabilitating the patient's feet or lower limbs; an upper-limb traction means 4 adjacent to the patient's head side A and connected to the rotary traction means 3 and simultaneously driven by the rotary traction means 3 and driving means 2 for reciprocatively exercising or rehabilitating the patient's hands or upper limbs; and a lower-limb traction means 5 adjacent to the patient's feet side B and connected to the rotary traction means 3, and simultaneously driven by the rotary traction means 3 and driving means 2 for reciprocatively exercising or rehabilitating the patient's lower limbs.

The traction means 3, 4 or 5 of the present invention is respectively provided for traction of the patient's upper and lower limbs in a passive way as driven by the driving means 2.

The bed 1 includes: a bed mattress 10 mounted on a bed frame to be ridden by a patient P, a feet-side mattress 10*a* detachably mounted on the bed frame adjacent to the patient's feet side B when the feet are ridden on the bed 1, and a base 1*a* for securing the driving means 2 thereon.

The driving means 2 is substantially a driving motor 21, such as an electric motor, a pneumatic or hydraulic motor, and includes a speed reducer 22 connected to the driving motor 21 for reducing a rotation speed of the motor shaft; a crank shaft 23 axially secured to the speed reducer 22; a right crank arm 24 and a left crank arm 25 separated at an angle of 180 degrees and respectively secured to opposite ends of the crank shaft 23 to be driven for rotation by the crank shaft 23, like the rotation of a pair of bicycle pedals oppositely mounted to the crank shaft of a bicycle chain wheel.

Figure 6:
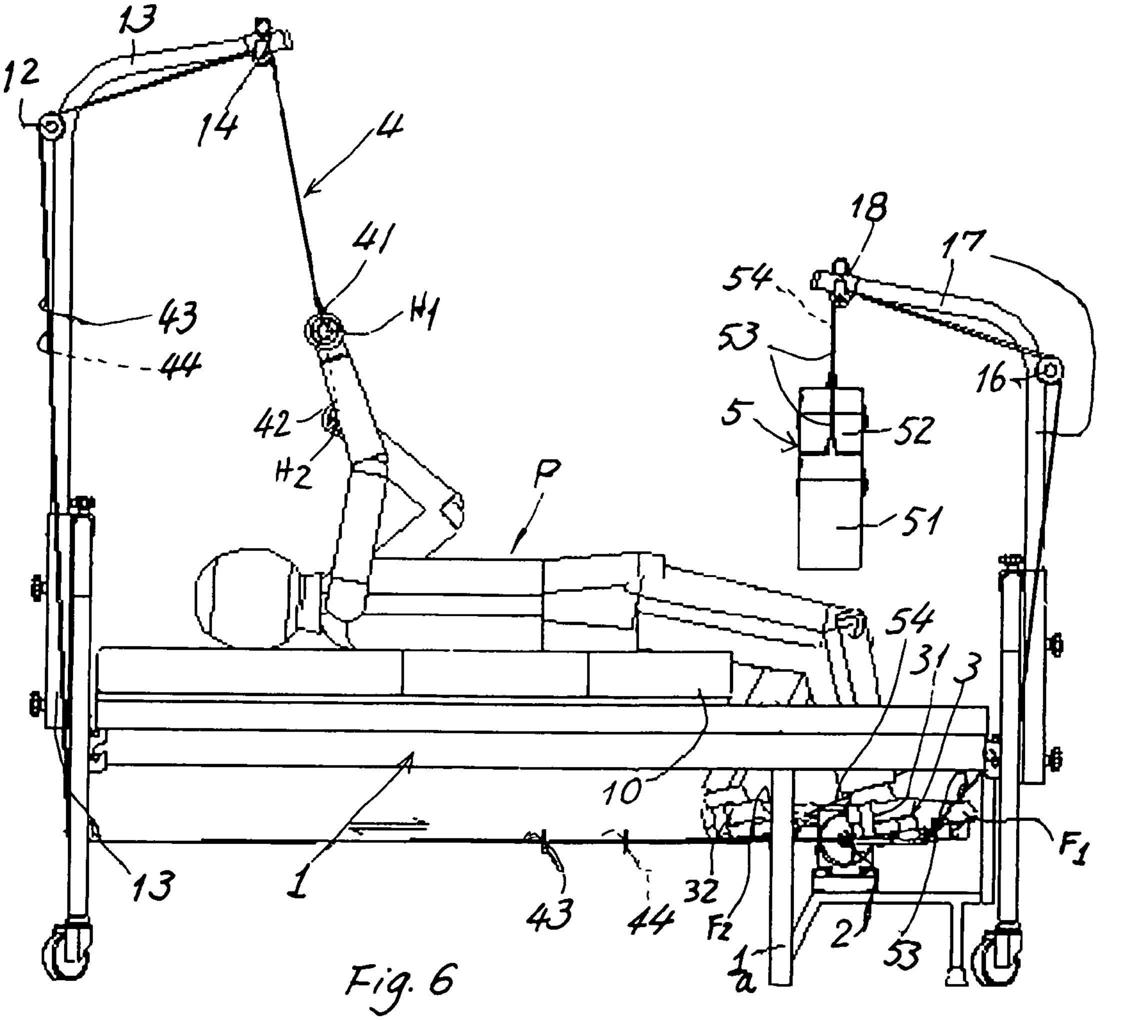
FIG. 6 is an illustration showing rehabilitation for alternately reciprocating a patient's upper limbs and for rotatably exercising the patient's feet by the present invention.

The rotary traction means 3 includes: a right pedal (or right-foot shoe) 31 pivotally secured to the right crank arm 24 of the driving means 2, a left pedal (or left-foot shoe) 32 pivotally secured to the left crank arm 25 of the driving means 2; with the rotary traction means 3 positioned at the patient's feet side B as corresponding to the feet-side mattress 10*a* of the bed 1, whereby upon removal of the feet-side mattress 10*a*, the patient's feet will be downwardly rested on the right and left pedals 31, 32 to be rotatably rehabilitated or exercised by the rotary traction means 3 (FIG. 6).

The upper-limb traction means 4 includes: a right-hand grip 41 connected to a rear end 311 of the right pedal 31 through a right rope 43 and a plurality of right pulleys (or rollers) 45, 45*a*, 45*b* to be operatively reciprocated as upwardly pulled by the right pedal 31 or gravitationally descending when not pulled by the right pedal 31 for reciprocating the patient's right hand H1 upwardly or downwardly; and a left-hand grip 42 connected to a rear end 321 of the left pedal 32 through a left rope 44 and a plurality of left pulleys 46, 46*s*, 46*b* to be operatively reciprocated as upwardly pulled by the left pedal 32 or gravitationally descending when not pulled by the left pedal 32 for reciprocating the patient's left hand H2 upwardly or downwardly.

The lower-limb traction means 5 includes: a right-foot strap (or holder) 51 connected to a front end 312 of the right pedal 31 through a right cable 53 (which is designated as right "cable" 53 in order to be distinguishable from the right "rope" 43 even they are made of the same or equivalent rope or cable materials) and a plurality of right pulleys 55, 55*a*, 55*b* to be operatively reciprocated as upwardly pulled by the right pedal 31 or gravitationally descending when not pulled by the right pedal 31 for reciprocating the patient's right foot F1 upwardly or downwardly; and a left-foot strap 52 connected to a front end 322 of the left pedal 32 through a left cable 54 and a plurality of left pulleys 56, 56*a*, 56*b* to be operatively reciprocated as pulled upwardly by the left pedal 32 or gravitationally descending when not pulled by the left pedal 32 for reciprocating the patient's left foot F2 upwardly or downwardly.

The right rope 43 includes a first right-rope end 431 pivotally secured to a rear end 311 of the right pedal 31, and a second right-rope end 432 secured to the right-hand grip 41; with the right rope 43 reciprocatively wound respectively about a head-side top right pulley 45 rotatably mounted on a head-side top bar 14 transversely formed on a top portion of a head column 13 formed on the bed 1, about a head-side upper right pulley 45*a* rotatably mounted on a head-side upper bar 12 (next to the top bar 14) transversely formed on an upper portion of the head column 13, and about a bottom right pulley 45*b* rotatably mounted on a bottom bar 11 transversely formed on a bottom portion of the bed 1.

The left rope 44 includes a first left-rope end 441 pivotally secured to a rear end 321 of the left pedal 32, and a second left-rope end 442 secured to the left-hand grip 42; with the left rope 44 reciprocatively wound respectively about a head-side top left pulley 46 rotatably mounted on the head-side top bar 14, about a head-side upper left pulley 46*a* rotatably mounted on the upper bar 12, and about a bottom left pulley 46*b* rotatably mounted on the bottom bar 11.

The first end 431 or 441 of the rope 43 or 44 may be modified to be pivotally secured to a radial end portion (not shown) of the crank arm 24.

Meanwhile, the right cable 53 or 54 may also be modified to be pivotally secured to a radial end portion (not shown) of another crank arm 25.

The right cable 53 includes a first right-cable end 531 pivotally secured to a front end 312 of the right pedal 31, and a second right-cable end 532 secured to the right-foot strap 51; with the right cable 53 reciprocatively wound respectively about a foot-side top right pulley 55 rotatably mounted on a foot-side top bar 18 transversely formed on a top portion of a foot column 17 formed on the bed 1, about a foot-side upper right pulley 55*a* rotatably mounted on a foot-side upper bar 16 (next to the top bar 18) transversely formed on an upper portion of the foot column 17, and about a lower right pulley 55*b* rotatably mounted on a lower bar 15 transversely formed on a lower portion of the bed 1 (at feet side B).

The left cable 54 includes a first left-cable end 541 pivotally secured to a front end 322 of the left pedal 32, and a second left-cable end 542 secured to the left-foot strap 52; with the left cable 54 reciprocatively wound respectively about a head-side top left pulley 46 rotatably mounted on the foot-side top bar 18, about a foot-side upper left pulley 56*a* rotatably mounted on the upper bar 16, and about a lower left pulley 56*b* rotatably mounted on the lower portion of the bed 1.

When the driving means 2 is started to rotate the two crank arms 24, 25, the two pedals 31, 32 will be rotated to rotate the patient's right foot F1 and left foot F2 to thereby rehabilitate or exercise his or her feet as shown in FIG. 6. The hand grips 41, 42 will be simultaneously and respectively reciprocated as rotatably driven by the two pedals 31, 32 and two crank arms 24, 25 of the driving means 2 to thereby rehabilitate or exercise the patient's right and left hands H1, H2.

Reviewing FIG. 6, when the right pedal 31 has been rotated to its front extremity, the right rope 43 has been driven by the pedal 31 to thereby pull the patient's right hand H1 upwardly just reaching the position as shown in FIG. 6; and the left pedal 32 has been rotated to its rear extremity, the left rope 44 is loosened (not pulled by pedal 32) to thereby gravitationally descend the left hand grip 42 and the patient's left hand H2 downwardly. (Note: In FIG. 6, the feet-side mattress 10*a* is removed to allow the patient's feet F1, F2 to be pendently rotated by the traction means 3).

After continuous rotation of the driving means 2 and the crank arms 24, 25, the pedals 31, 32 will be rotated to raise the left hand H2 (from FIG. 6) and to lower the right hand H1 alternately to thereby reciprocate the patent's hands H1, H2 for his (or her) hand rehabilitation or exercising.

Meanwhile, the patient's feet F1, F2 are passively rotated by the pedals 31, 32 as rotated by the crank arms 24, 25 of the driving means 2 to thereby perform a rotary traction or rehabilitation for his (or her) feet or lower limbs.

Figure 7:
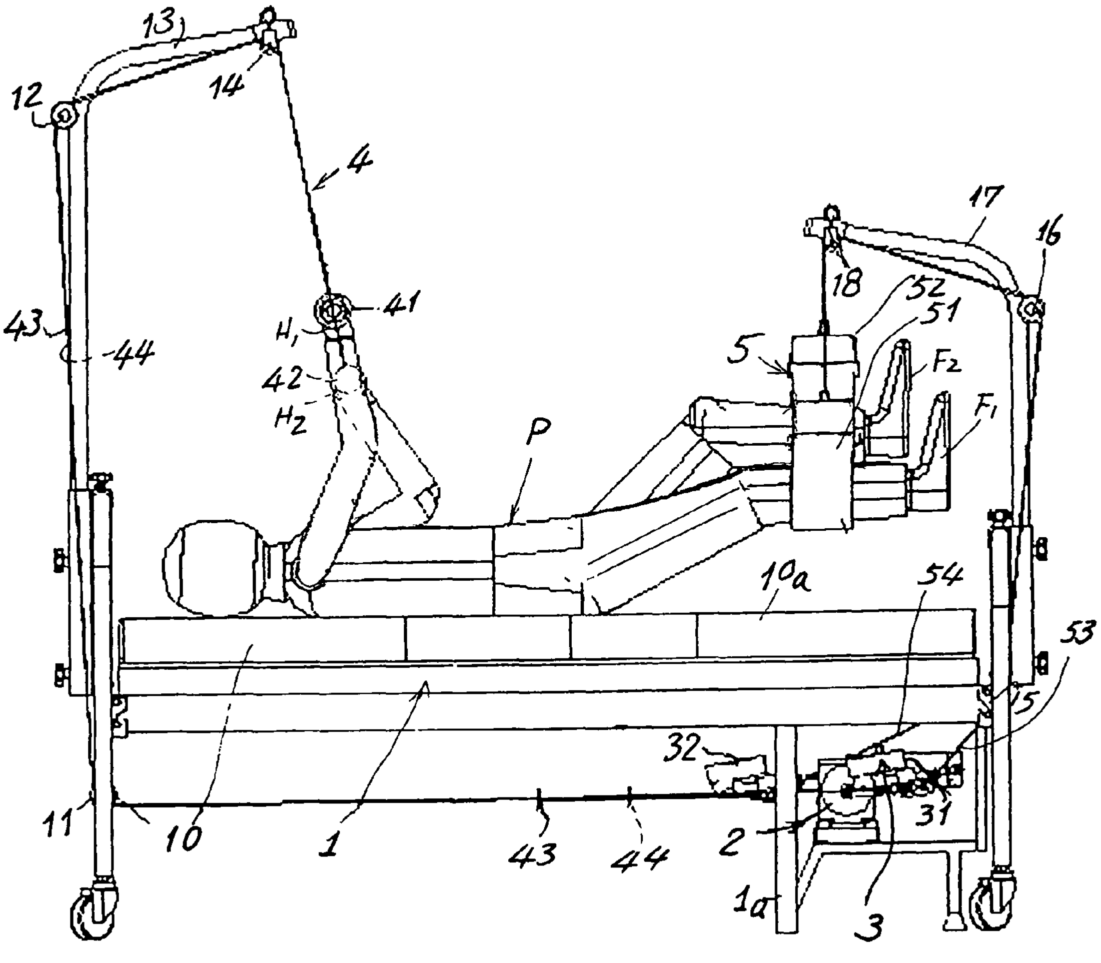
FIG. 7 shows rehabilitation both for patient's upper and lower limbs in alternately reciprocating movements.

As shown in FIG. 7, the patient's feet F1, F2 are held on the straps 51, 52. Just at this moment, the right pedal 31 has been rotated to the front extremity to loosen the right cable 53 to gravitationally descend the right foot F1 while the right rope 43 is pulled to thereby pull the right-hand grip 41 upwardly. Continuously, the left pedal 32 is rotated forwardly from its rear extremity towards its front extremity to pull the left-hand grip 42 and left hand H2 upwardly while the left cable 54 is loosened to descend the left strap 52 and left foot F2. Meanwhile, the right pedal 31 is simultaneously rotated rearwardly from its front extremity towards its rear extremity to pull the right cable 53 to raise the right strap 51 and right foot F1 while the right rope 43 is loosened to thereby descend the right-hand grip 41 and right hand H1. By the way, both hands H1, H2 (and upper limbs) and feet F1, F2 (and lower limbs) of the patient P will be alternately reciprocatively rehabilitated or exercised.

Figure 8:
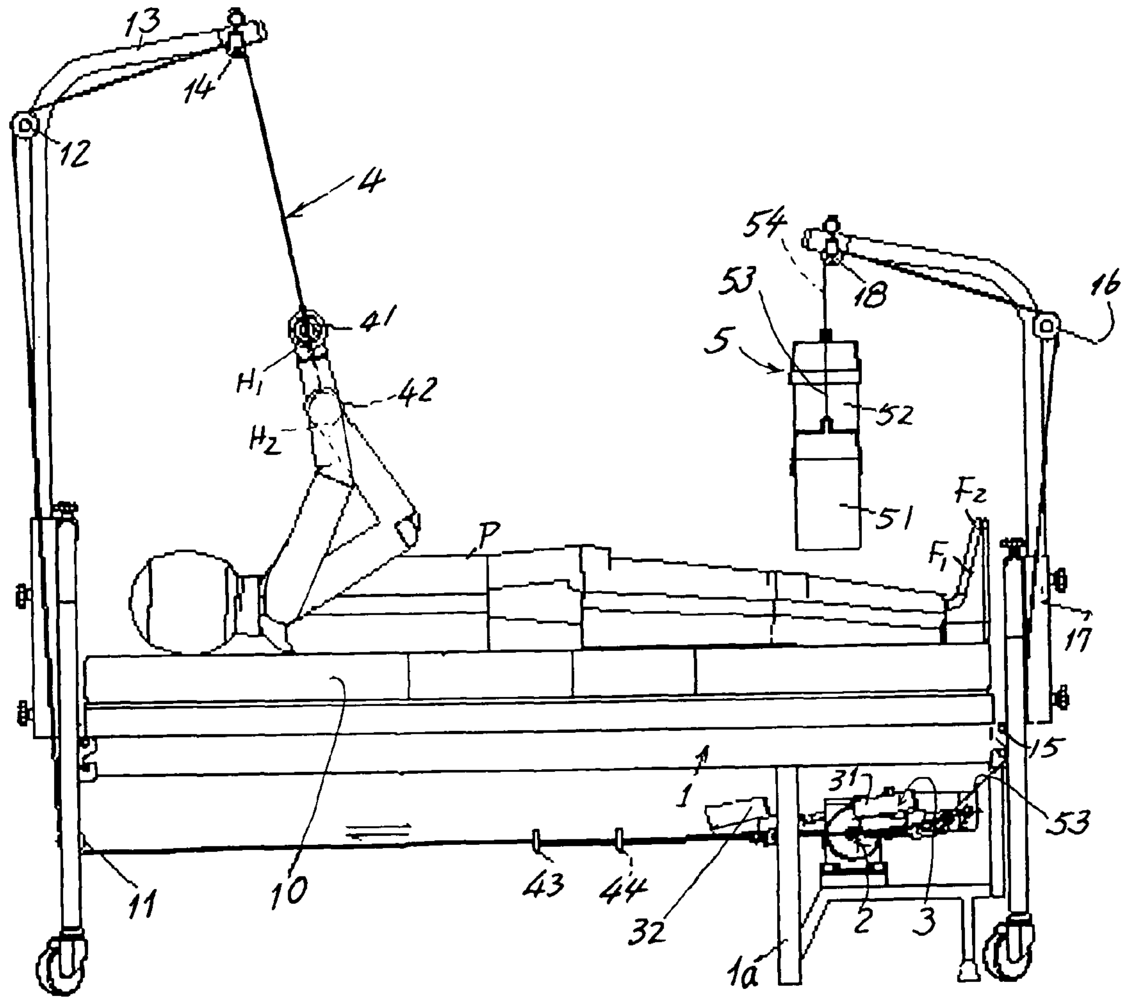
FIG. 8 shows rehabilitation of the patient's upper limbs while resting the lower limbs on the bed.

As shown in FIG. 8, only the patient's hands H1, H2 are rehabilitated, while his (or her) feet F1, F2 are rested upon the bed 1.

Figure 9:
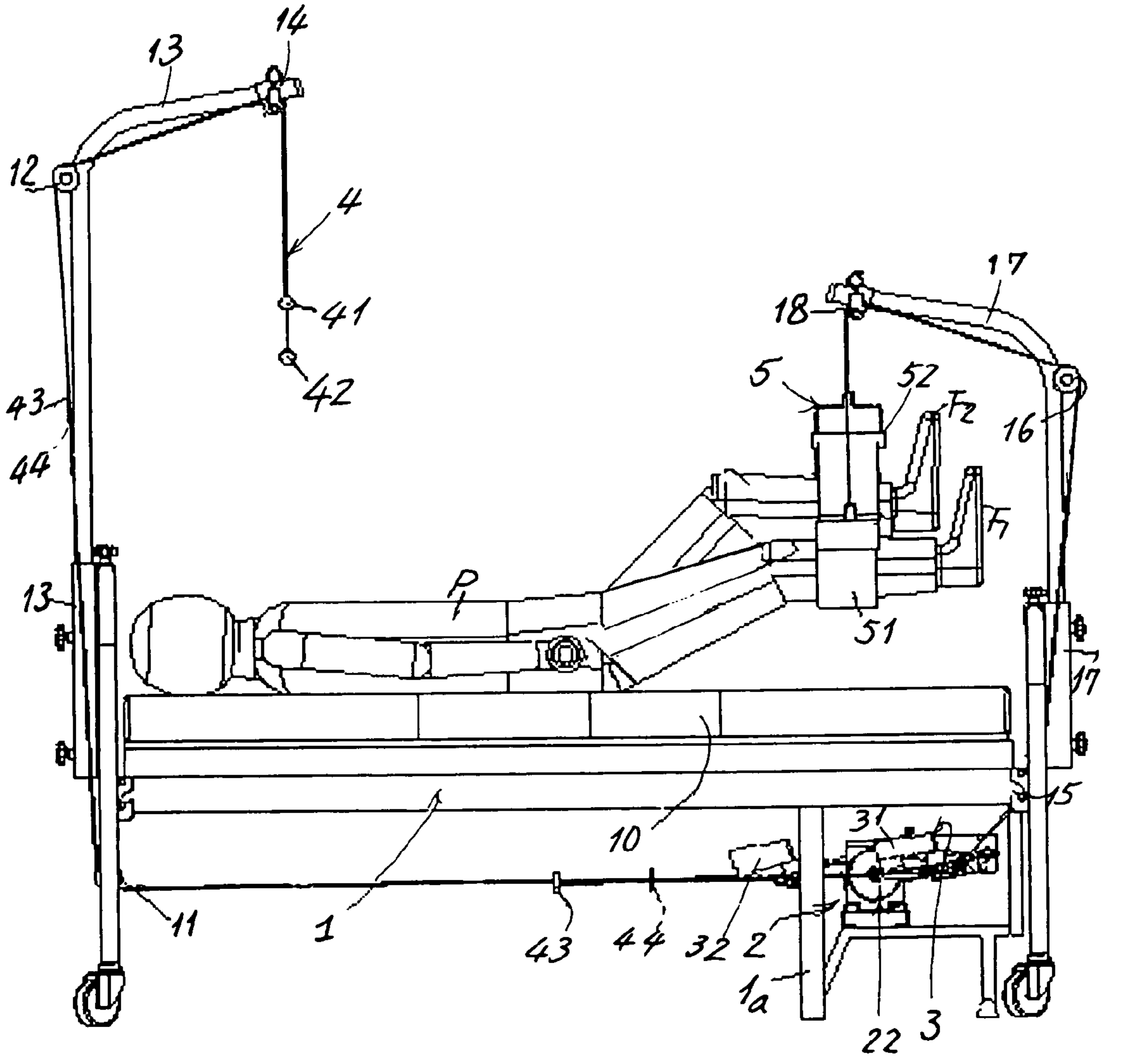
FIG. 9 shows rehabilitation of the patient's lower limbs while resting the upper limbs on the bed.

As shown in FIG. 9, only the patient's feet F1, F2 are rehabilitated, while the hands are taking a rest.

The present invention is superior to the prior art, because it may be provided to reciprocatively rehabilitate (or exercise) the patient's hands (or upper limbs) and feet (or lower limbs) simultaneously; and also to rotatably rehabilitate (or exercise) his (or her) feet while simultaneously reciprocatively rehabilitating the hands.

So, the present invention provide multiple rehabilitation and exercise functions and choices for the patients or users. For instance, when he is tired or bored for reciprocating his feet (FIG. 7), he may change his exercise "mode" to be a rotary traction as shown in FIG. 6.

The present invention may be further modified without departing from the scope and spirit of the present invention.

We claim:

1. A rehabilitation and exerciser bed comprising:

a bed; a driving means mounted on a bottom portion of the bed adjacent to a patient's feet side; a rotary traction means connected to and rotatably driven by the driving means for rotatably exercising or rehabilitating the patient's feet or lower limbs; an upper-limb traction means adjacent to the patient's head side and connected to the rotary traction means and simultaneously driven by the rotary traction means and the driving means for reciprocatively exercising or rehabilitating the patient's hands or upper limbs; and a lower-limb traction means adjacent to the patient's feet side and connected to the rotary traction means, and simultaneously driven by the rotary traction means and the driving means for reciprocatively exercising or rehabilitating the patient's lower limbs;

said rotary traction means including: a right pedal pivotally secured to a right crank arm of the driving means, a left pedal pivotally secured to a left crank arm of the driving means; with the rotary traction means positioned at a patient's feet side, whereby upon removal of a feet-side mattress, the patient's feet will be downwardly held on the right and left pedals to be rotatably rehabilitated or exercised by the rotary traction means; said upper-limb traction means including: a right-hand grip connected to a rear end of the right pedal of the rotary traction means through a right rope and a plurality of right pulleys to be operatively reciprocated as upwardly pulled by the right pedal or gravitationally descending when not pulled by the right pedal for reciprocating the patient's right hand upwardly or downwardly; and a left-hand grip connected to a rear end of the left pedal of said rotary traction means through a left rope and a plurality of left pulleys to be operatively reciprocated as upwardly pulled by the left pedal or gravitationally descending when not pulled by the left pedal for reciprocating the patient's left hand upwardly or downwardly; and said lower-limb traction means including: a right-foot strap connected to a front end of the right pedal of said rotary traction means through a right cable and a plurality of right pulleys to be operatively reciprocated as upwardly pulled by the right pedal or gravitationally descending when not pulled by the right pedal for reciprocating the patient's right foot upwardly or downwardly; and a left-foot strap connected to a front end of the left pedal of said rotary traction mean through a left cable and a plurality of left pulleys to be operatively reciprocated as pulled upwardly by the left pedal or gravitationally descending when not pulled by the left pedal for reciprocating the patient's left foot upwardly or downwardly.

2. A rehabilitation and exercise bed according to claim 1, wherein said bed includes: a bed mattress mounted on a bed frame to be ridden by a patient, a feet-side mattress, detachably mounted on the bed frame adjacent to the patient's feet side when the feet are ridden on the bed, and a base for securing the driving means thereon.

3. A rehabilitation and exercise bed according to claim 1, wherein said driving means includes a driving motor, a speed reducer connected to the driving motor for reducing a rotation speed of the motor; a crank shaft axially secured to the speed reducer; a right crank arm and a left crank arm separated at an angle of 180 degrees and respectively secured to opposite ends of the crank shaft to be driven for rotation by the crank shaft.

4. A rehabilitation and exercise bed according to claim 1, wherein each said rope includes a first rope end pivotally secured to a rear end of the pedal, and a second rope end secured to the hand grip; with the rope reciprocatively wound respectively about a head-side top pulley rotatably mounted on a head-side top bar transversely formed on a top portion of a head column formed on the bed, about a head-side upper pulley rotatably mounted on a head-side upper bar transversely formed on an upper portion of the head column, and about a bottom pulley rotatably mounted on a bottom bar transversely formed on a bottom portion of the bed.

5. A rehabilitation and exercise bed according to claim 1, wherein each said cable includes a first cable end pivotally secured to a front end of the pedal, and a second cable end secured to the foot strap; with the cable reciprocatively wound respectively about a foot-side top pulley rotatably mounted on a foot-side top bar transversely formed on a top portion of a foot column formed on the bed, about a foot-side upper pulley rotatably mounted on a foot-side upper bar transversely formed on an upper portion of the foot column, and about a lower pulley rotatably mounted on a lower bar transversely formed on a lower portion of the bed.

* * * * *